US010766835B2

(12) United States Patent
Van Willigenburg

(10) Patent No.: US 10,766,835 B2
(45) Date of Patent: Sep. 8, 2020

(54) SYSTEM AND METHOD FOR SEPARATION OF PROPYLENE AND PROPANE

(71) Applicant: SABIC GLOBAL TECHNOLOGIES B.V., Bergen op Zoom (NL)

(72) Inventor: Joris Van Willigenburg, Geleen (NL)

(73) Assignee: SABIC GLOBAL TECHNOLOGIES B.V., Bergen op Zoom (NL)

( * ) Notice: Subject to any disclaimer, the term of this patent is extended or adjusted under 35 U.S.C. 154(b) by 0 days.

(21) Appl. No.: 16/330,850

(22) PCT Filed: Aug. 21, 2017

(86) PCT No.: PCT/IB2017/055047
§ 371 (c)(1),
(2) Date: Mar. 6, 2019

(87) PCT Pub. No.: WO2018/047030
PCT Pub. Date: Mar. 15, 2018

(65) Prior Publication Data
US 2019/0202757 A1    Jul. 4, 2019

(30) Foreign Application Priority Data

Sep. 7, 2016 (EP) .................................... 16187525

(51) Int. Cl.
*C07C 7/04* (2006.01)
*B01D 3/14* (2006.01)
(Continued)

(52) U.S. Cl.
CPC ................ *C07C 7/005* (2013.01); *B01D 1/28* (2013.01); *B01D 3/007* (2013.01); *B01D 3/14* (2013.01); *C07C 7/04* (2013.01); *C07C 7/09* (2013.01)

(58) Field of Classification Search
None
See application file for complete search history.

(56) References Cited

U.S. PATENT DOCUMENTS

| 2,769,309 A | * | 11/1956 | Irvine | .................... | B01D 3/007 |
| | | | | | 62/623 |
| 2010/0025218 A1 | * | 2/2010 | Panditrao | ............... | C10G 45/00 |
| | | | | | 203/26 |

(Continued)

FOREIGN PATENT DOCUMENTS

| CN | 102728089 | 10/2012 |
| CN | 202777870 | 3/2013 |

(Continued)

OTHER PUBLICATIONS

International Search Report and Written Opinion issued in International Patent Application No. PCT/IB2017/055047, dated Nov. 20, 2017.

(Continued)

*Primary Examiner* — Philip Y Louie
(74) *Attorney, Agent, or Firm* — Norton Rose Fulbright US LLP

(57) ABSTRACT

A separation system for separating a feed stream comprising propylene and propane and a method for separating such feed stream. The separation system includes a distillation column for producing a light stream comprising propylene and a heavy stream comprising propane; a reboiler for reboiling a part of the first heavy stream to produce a boiled heavy stream; a condenser for cooling the light stream to produce a condensed light stream; and an absorption refrigerator for receiving water and providing chilled water, for receiving hot water from a waste heat source and providing a cooled hot water and for receiving cooling water and providing a heated cooling water. The absorption refrigerator is arranged such that the cooling of the water and the hot water occurs by the cooling water. The condenser is arranged such that the cooling of the light stream occurs by the chilled water from the absorption refrigerator.

19 Claims, 3 Drawing Sheets

(51) Int. Cl.
*C07C 7/00* (2006.01)
*B01D 3/00* (2006.01)
*C07C 7/09* (2006.01)
*B01D 1/28* (2006.01)

(56) References Cited

U.S. PATENT DOCUMENTS

2011/0041549 A1* 2/2011 Van DerSchrick .... B01D 3/007
  62/620
2011/0049051 A1 3/2011 Cougard et al.

FOREIGN PATENT DOCUMENTS

EP 2018899 1/2009
WO WO 2012/012153 1/2012

OTHER PUBLICATIONS

Zimmerman & Walzi, "Ethylene" Ullmann's Encyclopedia of Industrial Chemistry, 2012, vol. 13, pp. 465-529. (Updated Verison).

* cited by examiner

SYSTEM AND METHOD FOR SEPARATION OF PROPYLENE AND PROPANE

CROSS-REFERENCE TO RELATED APPLICATIONS

This application is a national phase under 35 U.S.C. § 371 of International Application No. PCT/IB2017/055047, filed Aug. 21, 2017, which claims the benefit of priority of European Patent Application No. 16187525.7, filed Sep. 7, 2016, the contents of each of which are hereby incorporated by reference in their entirety.

FIELD OF THE INVENTION

The invention relates to a separation system for separating a feed stream comprising propylene and propane. The invention further relates to a method for separating such feed stream.

BACKGROUND OF THE INVENTION

Separation of propylene (propene) from propane is well-known, as described in Zimmermann, H. and Walzl, R., 2009, Ethylene. Ullmann's Encyclopedia of Industrial Chemistry. Propylene fractionation separates propylene as a chemical-grade overhead product (typically 93-95 wt % min.) or more frequently as polymer-grade propylene (≥98 wt %) from propane. Separation to polymer grade propylene requires typically 150-230 stages and a reflux ratio of 20 because of the close boiling points of propylene and propane. One of the basic processes applied for this difficult separation task is operating polymer-grade fractionators at ca 1800 kPa, with cooling water in the overhead condenser and hot quench water in the reboiler. In the case of naphtha cracking and where sufficient waste heat is available from the hot quench water cycle this is the most economic process.

The condenser should operate at the lowest pressure that can be achieved by the cooling water, since a lower pressure leads to lowering of the cost. The cooling water typically has a temperature of 20-30° C. An example of a known separation system for separating a feed stream comprising propylene and propane is illustrated in FIG. 1.

In the example of FIG. 1, 20 t/h of liquid C3 product 101, containing 5% wt propane and 95% wt propylene, is fed to stage 78 of a distillation column C-101, which has 160 stages and a diameter of 4 meter. The pressure drop over the column C-101 is 1.3 bar. A reboiler H-101 has a duty of 18.8 $MW_{th}$ and produces 235 t/h of vapor 103. The distillation column C-101 produces 215 t/h of vapor 104 at the top that is condensed against cooling water in a condenser H-102, which is sent to vessel V-101. In the vessel V-101, 196 t/h of the condensed vapor is pumped back as a reflux 109 and 19 t/h of 99% pure propylene is produced as a product stream 111. The heat from the condenser H-102 is rejected to cooling water having a temperature of 20-30° C. In this case, the condenser H-102 operates at a pressure of 16 $bar_a$. The column is operated at a vapor velocity of 79% of the flooding velocity. The high pressure of the condenser H-102 makes the distillation more difficult, requiring a large amount of reflux. To accommodate the high vapor and liquid flows in the column as a result of the large amount of reflux, the column diameter needs to be large in order to avoid flooding of the column.

Thus, for operating at a vapor velocity of 79% of the flooding velocity using cooling water of 20-30° C. as in this example, the condenser pressure becomes 16 $bar_a$, which limits the amount of the liquid C3 product 101 fed to stage 78 of the distillation column C-101 to 20 t/h.

One known way of decreasing the pressure of the condenser is the use of a compressor for the vapor from the distillation column. FIG. 2 illustrates a separation system for separating a feed stream comprising propylene and propane, wherein a compressor is used. In the example of FIG. 2, the vapor 204 comes out from the distillation column C-201 at 9 $bar_a$ and is compressed by K-201 to obtain a compressed vapor 205 of 14 $bar_a$. This compressed vapor 205 is fed to a heat exchanger H-201. In the heat exchanger H-201, the compressed vapor 205 provides heat to reboil liquid 202 from the distillation column C-201 to obtain 203. The compressed vapor 205 is condensed to obtain a stream 206. The stream 206 is then sent to a vessel V-201, where one part 208 of the stream 206 is pumped back as a reflux and one part 210 of the stream 206 is taken from the system as the propylene product stream. The disadvantage of this system is that it requires a compressor to work. The compressor requires high value energy, such as electricity (motor drive), or high pressure stream (steam turbine drive) to function.

OBJECTS OF THE INVENTION

It is an objective of the present invention to provide a system for separating a feed stream comprising propylene and propane in which the above-mentioned and/or other problems are solved.

SUMMARY OF THE INVENTION

Accordingly, the present invention provides a separation system for separating a feed stream comprising propylene and propane, the system comprising:

i) a distillation column for producing a light stream comprising propylene and a heavy stream comprising propane, ii) a reboiler for reboiling a part of the first heavy stream to produce a boiled heavy stream, iii) a condenser for cooling the light stream to produce a condensed light stream and iv) an absorption refrigerator for receiving water and providing chilled water by the vaporization of a circulating refrigerant, wherein the absorption refrigerator is arranged to receive hot water from a waste heat source to provide heat for the circulation of the refrigerant, and provide cooled hot water, wherein the condenser is arranged such that the cooling of the light stream occurs by the chilled water from the absorption refrigerator.

The terms "about" or "approximately" are defined as being close to as understood by one of ordinary skill in the art. In one non-limiting embodiment the terms are defined to be within 10%, preferably, within 5%, more preferably, within 1%, and most preferably, within 0.5%.

The terms "wt. %", "vol. %" or "mol. %" refers to a weight, volume, or molar percentage of a component, respectively, based on the total weight, the total volume, or the total moles of material that includes the component. In a non-limiting example, 10 moles of component in 100 moles of the material is 10 mol. % of component.

The term "substantially" and its variations are defined to include ranges within 10%, within 5%, within 1%, or within 0.5%.

The terms "inhibiting" or "reducing" or "preventing" or "avoiding" or any variation of these terms, when used in the claims and/or the specification, includes any measurable decrease or complete inhibition to achieve a desired result.

The term "effective," as that term is used in the specification and/or claims, means adequate to accomplish a desired, expected, or intended result.

The use of the words "a" or "an" when used in conjunction with the term "comprising," "including," "containing," or "having" in the claims or the specification may mean "one," but it is also consistent with the meaning of "one or more," "at least one," and "one or more than one."

The words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The process of the present invention can "comprise," "consist essentially of," or "consist of" particular ingredients, components, compositions, etc., disclosed throughout the specification.

In the context of the present invention, 13 embodiments are described. Embodiment 1 is a separation system for separating a feed stream comprising propylene and propane. The system includes a distillation column for producing a light stream comprising propylene and a heavy stream comprising propane, ii) a reboiler for reboiling a part of the first heavy stream to produce a boiled heavy stream, iii) a condenser for cooling the light stream to produce a condensed light stream and iv) an absorption refrigerator for receiving water and providing chilled water by the vaporization of a circulating refrigerant, wherein the absorption refrigerator is arranged to receive hot water from a waste heat source to provide heat for the circulation of the refrigerant, and provide cooled hot water, wherein the condenser is arranged such that the cooling of the light stream occurs by the chilled water from the absorption refrigerator. Embodiment 2 is the method for separating a feed stream comprising propylene and propane using the separation system according to embodiment 1, wherein the method includes the steps of a) feeding the feed stream to the distillation column and collecting a part of the first heavy stream from the separation system, b) feeding a part of the heavy stream to the reboiler and feeding back the boiled heavy stream to the distillation column and c) feeding back a part of the condensed light stream to the distillation column as reflux and collecting a part of the condensed light stream from the separation system. Embodiment 3 is the method according to embodiment 2, wherein the cooled hot water from the absorption refrigerator is fed to the reboiler for providing heat for producing the boiled heavy stream. Embodiment 4 is the method according to any one of embodiments 2 or 3, wherein the feed stream comprises 2-98 wt. % of propylene and 98-2 wt. % of propane with respect to the total feed stream. Embodiment 5 is the method according to any one of embodiments 2 or 3, wherein the feed stream comprises 40-70 wt. % of propylene and 60-40 wt. % of propane with respect to the total feed stream. Embodiment 6 is the method according to any one of embodiments 2 or 3, wherein the feed stream comprises 80-98 wt. % of propylene and 20-2 wt. % of propane with respect to the total feed stream. Embodiment 7 is the method according to any one of embodiments 2 to 6, wherein the feed stream is a product of a propane dehydrogenation process. Embodiment 8 is the method according to any one of claims 2 or 3, wherein the chilled water from the absorption refrigerator has a temperature of at most 10° C., for example 8-10° C. Embodiment 9 is the method according to any one of embodiments 2 or 7, wherein the chilled water from the absorption refrigerator has a temperature of at most 15° C., for example 13-15° C. Embodiment 10 is the method according to any one of embodiments 2 or 9, wherein the hot water has a temperature in the range of 70-95° C. Embodiment 11 is the method according to any one of embodiments 2 or 10, wherein the hot water is quench water which has been heated by means of heat recovery. Embodiment 12 is the method according to any one of embodiments 2 or 11, wherein the hot water is quench water used in a steam cracking process and has a temperature of 75-85° C. Embodiment 13 is the method according to any one of claim 2 or 12, wherein the part of the first heavy stream collected from the separation system includes at least 80 wt. % of propane and/or the part of the condensed light stream collected from the separation system comprises at least 98 wt. % of propylene.

Other objects, features and advantages of the present invention will become apparent from the following figures, detailed description, and examples. It should be understood, however, that the figures, detailed description, and examples, while indicating specific embodiments of the invention, are given by way of illustration only and are not meant to be limiting. Additionally, it is contemplated that changes and modifications within the spirit and scope of the invention will become apparent to those skilled in the art from this detailed description. In further embodiments, features from specific embodiments may be combined with features from other embodiments. For example, features from one embodiment may be combined with features from any of the other embodiments. In further embodiments, additional features may be added to the specific embodiments described herein.

DETAILED DESCRIPTION

Figure 1:
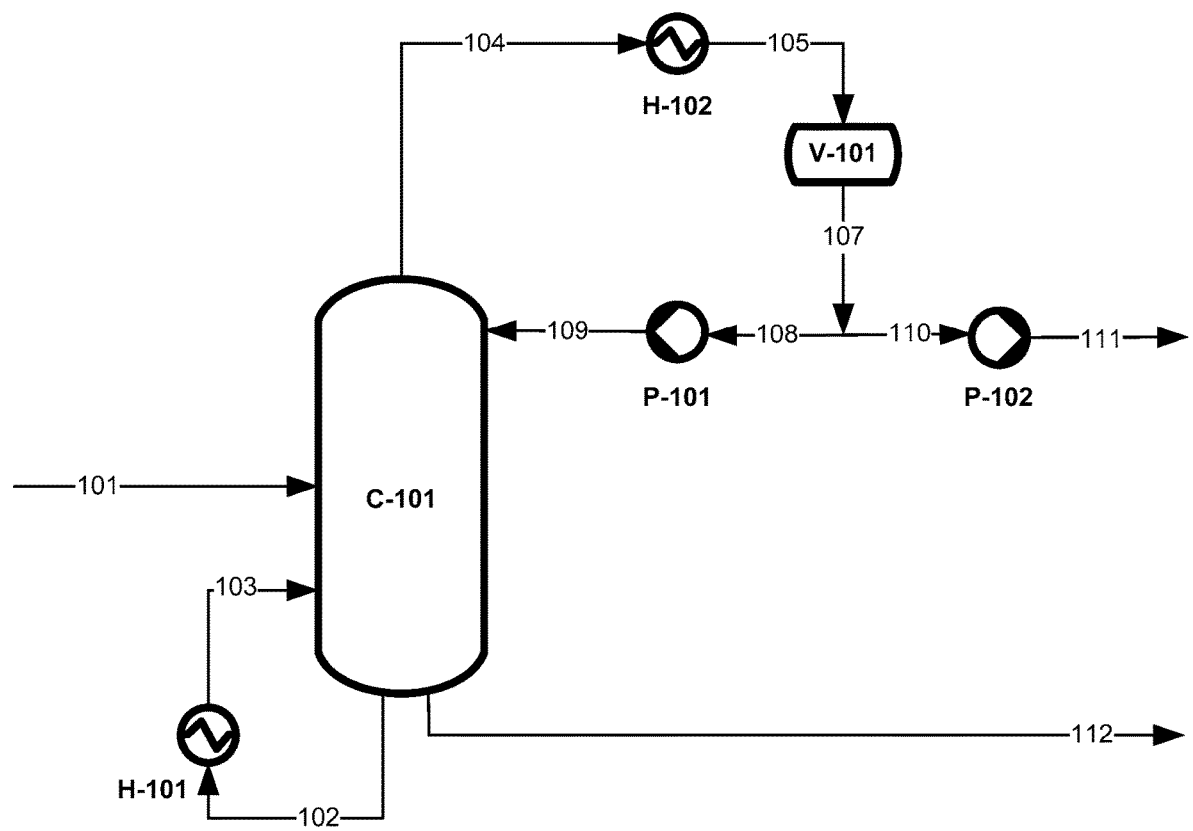
FIG. 1 is a prior art separation system for separating a feed stream comprising propylene and propane.

According to the present invention, the condenser is cooled by the chilled water provided by the absorption refrigerator, instead of cooling water typically having a temperature of 20-30° C. The absorption refrigerator uses hot water from a waste heat source for providing heat for the circulation of the refrigerant necessary for the operation of the absorption refrigerator. Accordingly, heat from a waste heat source is efficiently utilized for providing chilled water having a low temperature, e.g. of at most 15° C. Compared to other means for providing chilled water of such low temperature, the process according to the invention is energy efficient since heat from a waste heat source can be used. Other means for producing chilled water of such low temperature is a mechanical vapor compression cycle. This requires high quality energy to drive, such as electric power for an e-motor driven compressor or high pressure steam for a steam turbine driven compressor. In comparison, the process according to the invention advantageously uses an absorption refrigerator which is operated by low grade waste heat.

The invention further provides a method for separating a feed stream comprising propylene and propane using the separation system according to the invention, wherein the method comprises the steps of:

a) feeding the feed stream to the distillation column and collecting a part of the first heavy stream from the separation system, b) feeding a part of the heavy stream to the reboiler and feeding back the boiled heavy stream to the distillation column and c) feeding back a part of the condensed light stream to the distillation column as reflux and collecting a part of the condensed light stream from the separation system.

Preferably, the cooled hot water is fed to the reboiler for providing heat for producing the boiled heavy stream. This further improves energy efficiency of the system. The cooled hot water may be the only source for providing the heat for the reboiler. Alternatively, if the heat from the cooled hot water is insufficient in terms of temperature or amount, a further (low pressure) steam can be added to the reboiler for providing additional heat.

Feed Stream

Preferably, the feed stream comprises 2-98 wt. % of propylene and 98-2 wt. % of propane. Preferably, the total amount of propylene and propane is at least 95 wt. %, for example at least 98 wt. %, at least 99 wt. % or 100 wt. % of the total of the feed stream.

In some embodiments, the feed stream comprises 85-98 wt. % of propylene and 15-2 wt. % of propane. Such feed stream may be the C3 fraction from naphtha cracking or a product of a propane cracking.

In some embodiments, the feed stream comprises 40-70 wt. % of propylene and 60-40 wt. % of propane. Such feed stream may be a product of a propane dehydrogenation process.

Absorption Refrigerator

Absorption refrigerator is per se well-known. The absorption cooling cycle, like the mechanical vapor compression refrigeration cycle, utilizes the latent heat of evaporation of a refrigerant to remove heat from the entering chilled water. Vapor compression refrigeration systems use a refrigerant and a compressor to transport the refrigerant vapor to be condensed in the condenser. The absorption cycle, however, uses water as the refrigerant and an absorbent lithium bromide solution to absorb the vaporized refrigerant. Heat is then applied to the solution to release the refrigerant vapor from the absorbent. The refrigerant vapor is then condensed in the condenser.

The basic single-effect absorption cycle includes generator, condenser, evaporator and absorber with refrigerant (liquid) and lithium bromide as the working solutions. The generator utilizes a heat source (burner, steam or hot water) to vaporize the diluted lithium bromide solution. The water vapor that is released travels to the condenser where it is condensed back into a liquid, transferring the heat to the cooling tower water. Once condensed, the liquid refrigerant is distributed over the evaporator tubes, removing the heat from the chilled water and vaporizing the liquid refrigerant. The concentrated lithium bromide solution from the generator passes into the absorber, absorbs the refrigerant vapor solution from the evaporator and dilutes itself. The diluted lithium bromide solution is then pumped back to the generator where the cycle is started again.

According to the invention, heat for releasing the refrigerant vapor from the absorbent is provided by hot water from a waste heat source. Various waste heat sources can be used, e.g. the heat released from condensation of a stream in a reactor. Waste heat source can be the heat released from condensing the dilution steam and pyrolysis gasoline in the quench tower of a steam cracker effluent or the heat released from condensing the dilution steam in the case of the effluent of a propane dehydrogenation reactor effluent. Other suitable waste heat sources are the heat released from condensing the furnace flue gasses to as low as 80-90° C. and also capturing the energy from condensation of the water in the flue gas. The furnace flue gasses could be of steam cracking furnaces or of furnaces proving heat for the propane dehydrogenation reactors. Other suitable waste heat sources are the overhead condensers of the pyrolysis gasoline fractionating columns, in particular the de-hexanizer column overhead condenser. In a system for fractionating a hydrocarbon stream, successive distillation is commonly used. A hydrogenated stream of pygas is fractionated by successively using a debutanizer column, a depentanizer column, a dehexanizer column etc. The dehexanizer column provides a particularly large heat source for heat recovery.

Preferably, the chilled water from the absorption refrigerator has a temperature of at most 15° C., for example 13-15° C. More preferably, the chilled water from the absorption refrigerator has a temperature of at most 10° C., for example 8-10° C. The chilled water of 8-10° C. cools the light stream and returns to the absorption refrigerator e.g. at a temperature of 10-12° C.

Preferably, the hot water from a waste heat source has a temperature of 70-95° C., for example 75-85° C. Preferably, the hot water is quench water which has been heated by means of heat recovery from the condensing of dilution steam and pyrolysis gasoline in the quench tower of a steam cracker.

Preferably, the part of the first heavy stream collected from the separation system comprises at least 80 wt. % of propane, more preferably at least 90 wt. % of propane. Preferably, the part of the condensed light stream collected from the separation system comprises at least 98 wt. % of propylene, more preferably at least 99 wt. % of propylene.

It is noted that the invention relates to all possible combinations of features described herein, preferred in particular are those combinations of features that are present in the claims. It will therefore be appreciated that all combinations of features relating to the composition according to the invention; all combinations of features relating to the process according to the invention and all combinations of features relating to the composition according to the invention and features relating to the process according to the invention are described herein.

It is further noted that the term 'comprising' does not exclude the presence of other elements. However, it is also to be understood that a description on a product/composition comprising certain components also discloses a product/composition consisting of these components. The product/composition consisting of these components may be advantageous in that it offers a simpler, more economical process for the preparation of the product/composition. Similarly, it is also to be understood that a description on a process comprising certain steps also discloses a process consisting of these steps. The process consisting of these steps may be advantageous in that it offers a simpler, more economical process.

When values are mentioned for a lower limit and an upper limit for a parameter, ranges made by the combinations of the values of the lower limit and the values of the upper limit are also understood to be disclosed.

Figure 3:
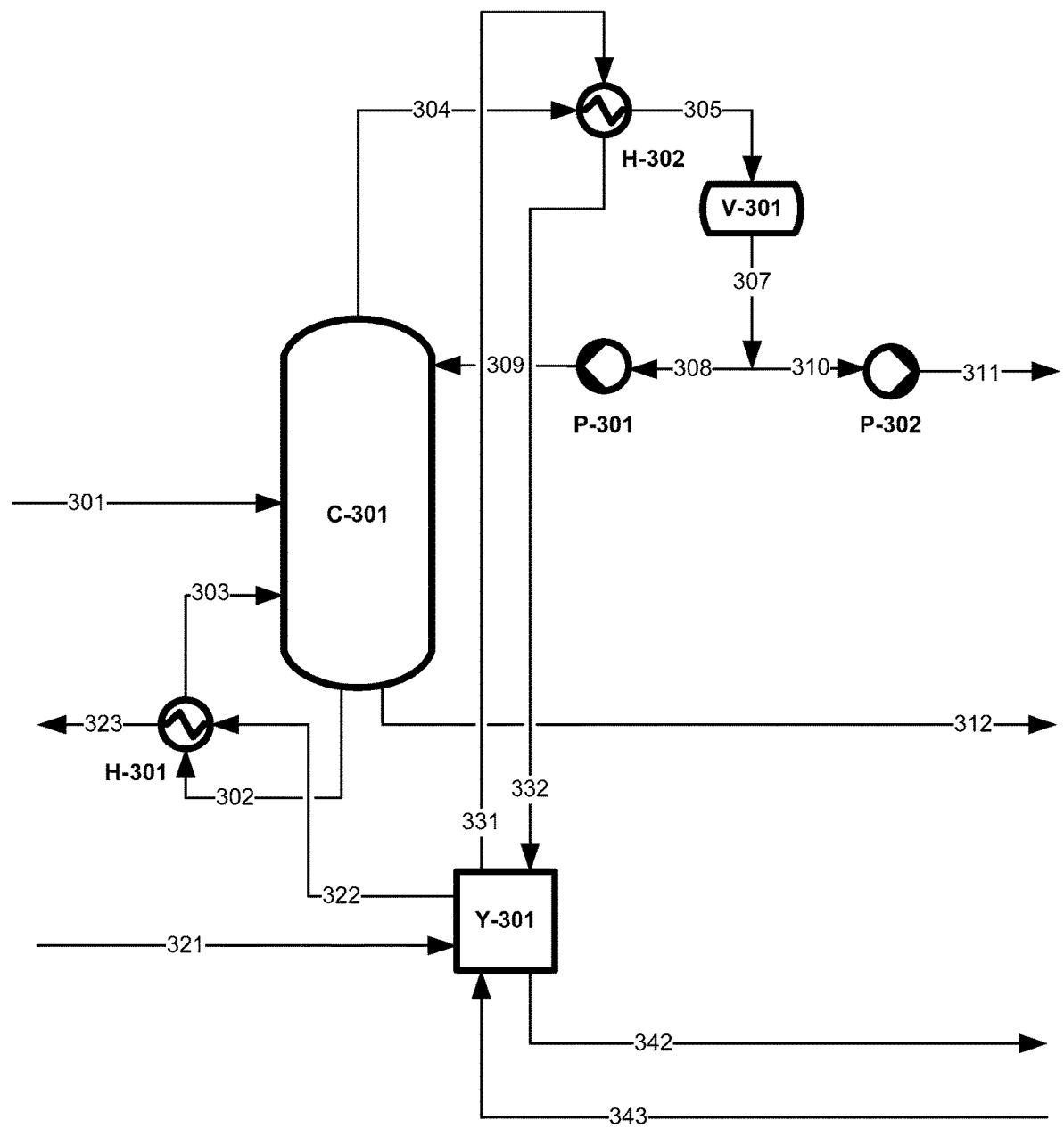
FIG. 3 schematically illustrates an embodiment of the separation system according to the present invention.

The invention is now further elucidated referring to the drawings in which FIG. 3 schematically illustrates an embodiment of the separation system according to the invention.

In the example of FIG. 3, 25.3 t/h of a liquid C3 product 301, containing 5% wt. propane and 95% wt. propylene, is fed to stage 78 of a distillation column C-301 which has 160 stages and a diameter of 4 meter. The pressure drop over the column is 1.3 bar. A reboiler H-301 has a duty of 21 MW$_{th}$ and produces 226 t/h of vapor 303. The distillation column C-301 produces 214 t/h of vapor 304 at the top that is condensed against chilled water in a condenser H-302, which is sent to vessel V-301. From the vessel—V-301, 190 t/h of the condensed vapor is pumped back as reflux 309 and 24 t/h of 99% pure propylene is produced as stream 311. The condenser H-302 operates at a pressure of 9 bar$_a$. The column is operated at a vapor velocity of 79% of the flooding velocity.

Absorption refrigerator Y-301 produces chilled water 331 at a temperature of approximately 8-10° C. and supplies this to H-302, which returns it at 10-12° C. The duty of H-302 is 21 MW$_{th}$. For the duty of 21 MW$_{th}$ of H-302, Y-301 requires 30 MW$_{th}$ of heat from quench water that is supplied at 80° C. by stream 321 and returned at 73° C. by stream 322. The used quench water can be further used for providing heat for the reboiler H-301, which reduces the temperature of the quench water by another 5° C. By cascading the quench water in this way, it can be used more efficiently. Cooling water necessary for the operation of the absorption refrigerator is indicated as 343, which comes out as 342.

Thus, for operating at a vapor velocity of 79% of the flooding velocity using cooling water of 8-10° C. as in this example, the condenser pressure becomes 9 bar$_a$, which allows the amount of the liquid C3 product 101 fed to stage 78 of the distillation column C-101 to be 25.3 t/h.

Figure 2:
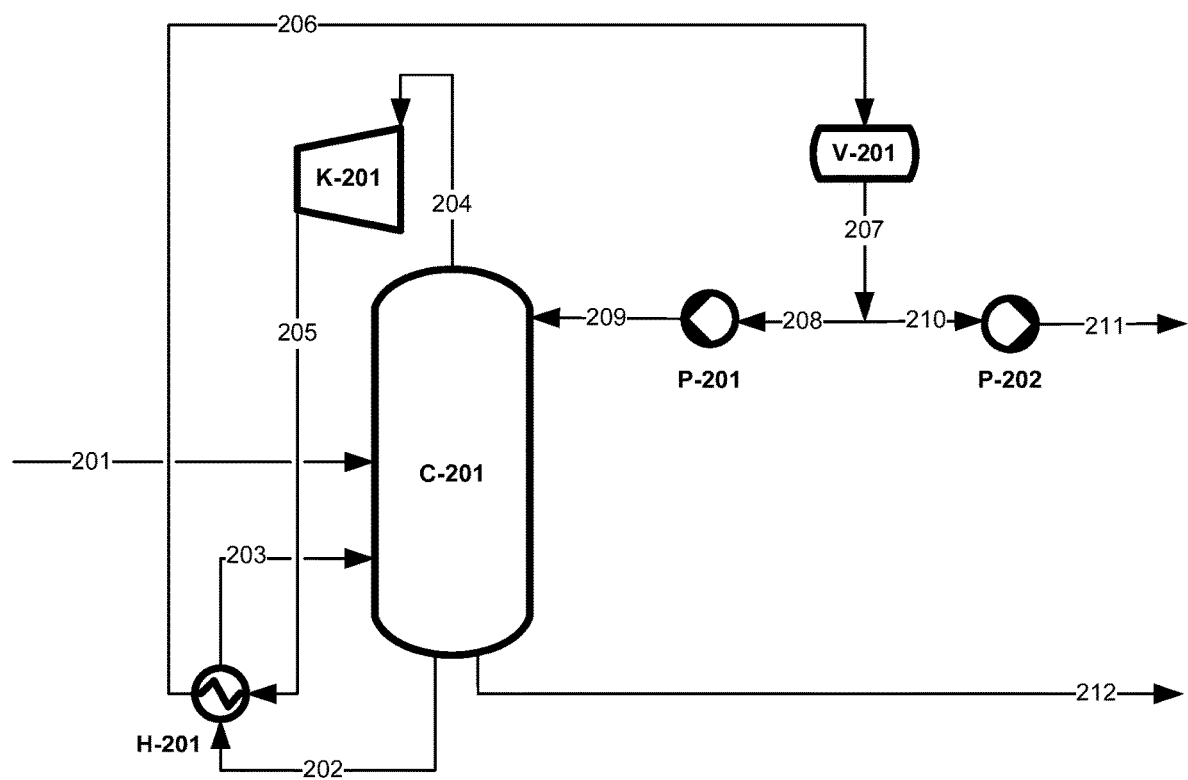
FIG. 2 illustrates a known separation system for separating a feed stream comprising propylene and propane, wherein a compressor is used.

Hence, the system illustrated in FIG. 3 has a higher capacity than the system illustrated in FIG. 1. Compared to the system illustrated in FIG. 1, the capacity has increased by (25.3−20)/20*100%=27%. Compared to the system illustrated in FIG. 2, the energy consumption and installation costs of the compressor K-201 are avoided.

It is claimed:

1. A method for separating a feed stream comprising propylene and propane using a separation system comprising:
   i) a distillation column for producing a light stream comprising propylene and a heavy stream comprising propane,
   ii) a reboiler for reboiling a part of the first heavy stream to produce a boiled heavy stream,
   iii) a condenser for cooling the light stream to produce a condensed light stream, and
   iv) an absorption refrigerator for receiving water and providing chilled water by the vaporization of a circulating refrigerant, wherein the absorption refrigerator is arranged to receive hot water from a waste heat source to provide heat for the circulation of the refrigerant, and provide cooled hot water,
   wherein the condenser is arranged such that the cooling of the light stream occurs by the chilled water from the absorption refrigerator, wherein the method comprises the steps of:
   a) feeding the feed stream to the distillation column and collecting a part of the first heavy stream from the separation system,
   b) feeding a part of the heavy stream to the reboiler and feeding back the boiled heavy stream to the distillation column and
   c) feeding back a part of the condensed light stream to the distillation column as reflux and collecting a part of the condensed light stream from the separation system;
   wherein the hot water is quench water.

2. The method according to claim 1, wherein the feed stream comprises 2-98 wt. % of propylene and 98-2 wt. % of propane with respect to the total feed stream.

3. The method according to claim 1, wherein the feed stream comprises 40-70 wt. % of propylene and 60-40 wt. % of propane with respect to the total feed stream.

4. The method according to claim 1, wherein the feed stream comprises 80-98 wt. % of propylene and 20-2 wt. % of propane with respect to the total feed stream.

5. The method according to claim 1, wherein the feed stream is a product of a propane dehydrogenation process.

6. The method according to claim 1, wherein the chilled water from the absorption refrigerator has a temperature of at most 10° C.

7. The method according to claim 1, wherein the chilled water from the absorption refrigerator has a temperature of at most 15° C.

8. The method according to claim 1, wherein the hot water has a temperature in the range of 70-95° C.

9. The method according to claim 1, wherein the quench water has been heated by means of heat recovery.

10. The method according to claim 1, wherein the quench water was used in a steam cracking process.

11. The method according to claim 1, wherein the part of the first heavy stream collected from the separation system comprises at least 80 wt. % of propane.

12. The method according to claim 1, wherein the quench water was used in a steam cracking process and has a temperature of 75-85° C.

13. The method according to claim 2, wherein the feed stream is a product of a propane dehydrogenation process.

14. The method according to claim 2, wherein the chilled water from the absorption refrigerator has a temperature of at most 10° C.

15. The method according to claim 2, wherein the chilled water from the absorption refrigerator has a temperature of at most 15° C.

16. The method according to claim 2, wherein the hot water has a temperature in the range of 70-95° C.

17. The method according to claim 2, wherein the quench water has been heated by means of heat recovery.

18. The method according to claim 2, wherein the part of the condensed light stream collected from the separation system comprises at least 98 wt. % of propylene.

19. A method for separating a feed stream comprising propylene and propane using a separation system comprising:
   i) a distillation column for producing a light stream comprising propylene and a heavy stream comprising propane,
   ii) a reboiler for reboiling a part of the first heavy stream to produce a boiled heavy stream,
   iii) a condenser for cooling the light stream to produce a condensed light stream, and
   iv) an absorption refrigerator for receiving water and providing chilled water by the vaporization of a circulating refrigerant, wherein the absorption refrigerator is arranged to receive hot water from a waste heat source to provide heat for the circulation of the refrigerant, and provide cooled hot water, wherein the condenser is arranged such that the cooling of the light stream occurs by the chilled water from the absorption refrigerator, wherein the method comprises the steps of:

a) feeding the feed stream to the distillation column and collecting a part of the first heavy stream from the separation system, b) feeding a part of the heavy stream to the reboiler and feeding back the boiled heavy stream to the distillation column and c) feeding back a part of the condensed light stream to the distillation column as reflux and collecting a part of the condensed light stream from the separation system, wherein the cooled hot water from the absorption refrigerator is fed to the reboiler for providing heat for producing the boiled heavy stream.

* * * * *